United States Patent [19]

Casey

[11] 4,053,237
[45] Oct. 11, 1977

[54] MEASURING THE SURFACE OF A ROLLER BY GLOSSMETER

[75] Inventor: Harry B. Casey, Covington, Va.

[73] Assignee: Westvaco Corporation, New York, N.Y.

[21] Appl. No.: 701,907

[22] Filed: July 2, 1976

[51] Int. Cl.² ............................................. G01N 21/48
[52] U.S. Cl. ............................. 356/209; 51/289 R; 264/209; 356/199; 356/210
[58] Field of Search ............... 356/210, 212, 199, 209, 356/237; 260/292, 295 Q; 264/216, 219; 51/289

[56] References Cited

U.S. PATENT DOCUMENTS

| 2,246,501 | 6/1941 | Braduer et al. | 356/199 |
| 3,512,894 | 5/1970 | Wood | 356/209 |
| 3,659,943 | 5/1972 | Godsby | 356/209 |
| 3,890,049 | 6/1975 | Collius et al. | 356/199 |

FOREIGN PATENT DOCUMENTS 2,258,617  8/1975  France ............................ 356/209

OTHER PUBLICATIONS

Atwill et al., Disposable Sheed for Instrument Head, vol. 19, No. 1, June 1976, pp. 188,189.

*Primary Examiner*—John K. Corbin
*Assistant Examiner*—B. W. de los Reyes
*Attorney, Agent, or Firm*—W. Allen Marcontell; Richard L. Schmalz

[57] ABSTRACT

The surface texture of plastic film cast against chill rolls may be accurately predicted from the roll surface texture while mounted in a roll finishing machine by correlating a glossmeter measurement of the roll surface to an experimentally determined functional relation between similar rolls and corresponding film product.

Means are provided on the glossmeter test base to assure accurate orientation of the instrument relative to the cylindrical surface and axis of the test subject.

3 Claims, 4 Drawing Figures

MEASURING THE SURFACE OF A ROLLER BY GLOSSMETER

BACKGROUND OF THE INVENTION

1. Field Of The Invention

The present invention relates to the manufacture of plastic film and of web materials coated with plastic film.

More particularly, the present invention relates to a method of testing the finish ground surface texture of chill rolls for plastic film extrusion machines and to apparatus for performing the test.

2. Description Of The Prior Art

In the manufacture of film products from thermoplastic polymer materials such as a polyethylene, polyvinychloride, polypropylene, polyesters, and ethylenevinyl acetates, it is known to extrude the plastic material in a viscous, molten state onto a rotating chill roll.

Similarly, web products such as paper are coated with such plastic films by extruding a molten flow of the material onto a traveling web of paper substrate. Immediately following contact with the paper web, the plastic is cooled by surface contact with a rotating chill roll.

Since the plastic is heated to a viscous, liquid state for extrusion, when the hot material initially contacts a chill roll, the roll surface texture is cast into the surface of the plastic. Consequently, the surface finish of a chill roll is the primary determinator for the surface finish of the final product.

The measurement of surface finish as a machine shop practice for the manufacture of roll elements is normally accomplished by means of an instrument known as a profile measuring device which determines the root mean square deviation of surface profile irregularities from an average surface plane. The disclosure of U.S. Pat. Nos. 3,253,370; 3,613,319; and 3,835,597 are directed at this method of roll finish measurement.

For measurement of paper, plastic and sheet product surface finish, however, the technique of spectral reflectance is used. This technique is defined by ASTM test method D523. Instruments for performing the ASTM test method D523, known as glossmeters, are described in U.S. Pat. Nos. 1,988,556; 2,063,551; 2,471,750; 2,739,246 and 3,549,264.

In practice, there has been little or no correlation found between the two test methods since a given profile measuring device for different surfaces may produce vastly different glossmeter measurements. This lack of correlation has generated considerable consternation with the plastic coated paper and film industries due to the fact that chill roll surfaces are frequently damaged in use. Such an event necessitates the need for roll surfacing refinishing. However, since there is no correlation between profile measuring device and glossmeter measurements, it is often necessary to install a refinished chill roll and make the desired product with it to determine that the finish texture of the product is incorrect. If incorrect, the subject roll must again be removed from the production machine for further finishing.

Analysis of the problem would seem to suggest that a glossmeter instrument should be used to monitor final finishing of a roll on the finish polishing machine. However, as heretofore understood, the operational principals of gloss measurement are predicated on lthe flatness of the test subject. This criterion is repeated throughout literature on the subject. The cylindrical surface of a chill roll obviously does not conform to the gloss measurement premise. Consequently, heretofore, the glossmeter was not known to the machinist.

SUMMARY OF THE INVENTION

It has been discovered that if a glossmeter instrument is positioned on a cyclindrical surface whereby the plane defined by the instrument incident and reflective light beam paths is in parallel coincidence with the cylinder axis, consistent reflectance measurements may be obtained.

Instrument base alignment means are provided to assure the necessary parallel coincidence.

By means of the above discovery, it has further been discovered that a consistent correlation may be defined between the surface texture of a steel chill roll and that of a plastic film surface cast thereagainst. In the case of the ASTM test method D523 for a 60° angle of incidence, the correlation was found to be substantially linear. Different angles of spectral incidence may be used for other, e.g. higher or lower, gloss ranges.

BRIEF DESCRIPTION OF THE DRAWING

Relative to the drawing wherein like reference characters designate like or similar elements throughout the several figures.

DESCRIPTION OF THE PREFERRED EMBODIMENT

Figure 1:
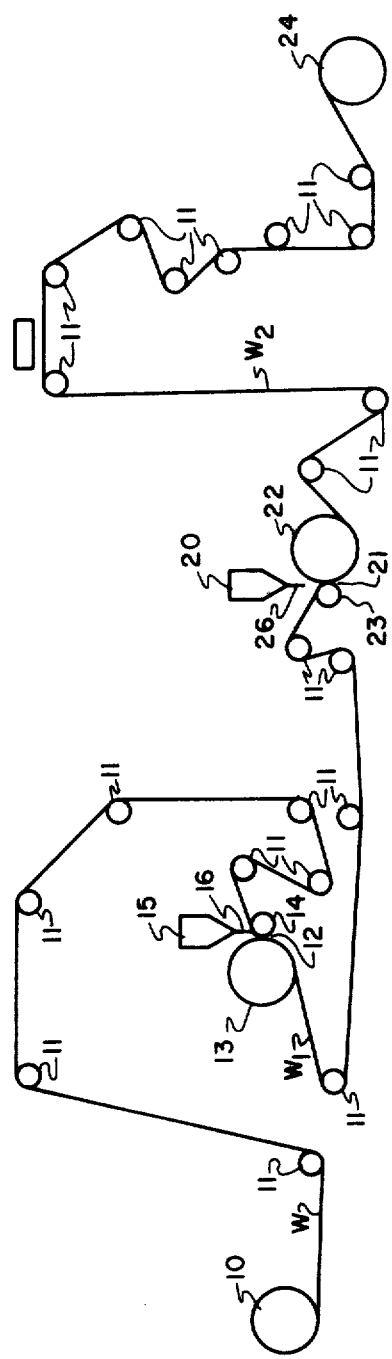
FIG. 1 is a line schematic of a machine for coating both surfaces of a paper web with hot, extruded plastic film.

To understand a representative application environment of the present invention, reference is made to FIG. 1 wherein the line schematic of a machine for coating the surfaces of a paper web substrate with hot, extruded plastic film is illustrated. From supply roll 10, a webof paperboard stock W is routed over idler rolls 11 into a nip 12 between a smooth surface, steel chill roll 13 and a rubber pressure roll 14, both of which are water cooled. Above the nip 12 is a hot plastic film extruder 15 which is positioned so the film flow stream 16 first engages the web W to be carried immediately thereafter into the nip 12 where it is chilled by surface contact with the chill roll 13.

Following the nip 12, the one side coated web $W_1$ passes over additional idler rolls 11 to reverse the surface positions so that the coated surface faces downward and the uncoated surface faces upward. A second coating of plastic 26 is applied by extruder 20 as the web $W_1$ passes through the nip 21 between a second, water cooled chill roll 22 and pressure roll 23. Web $W_2$ emerges from the nip 21 with plastic coating applied to both sides thereof and re-wound about reel 24.

Figure 2:
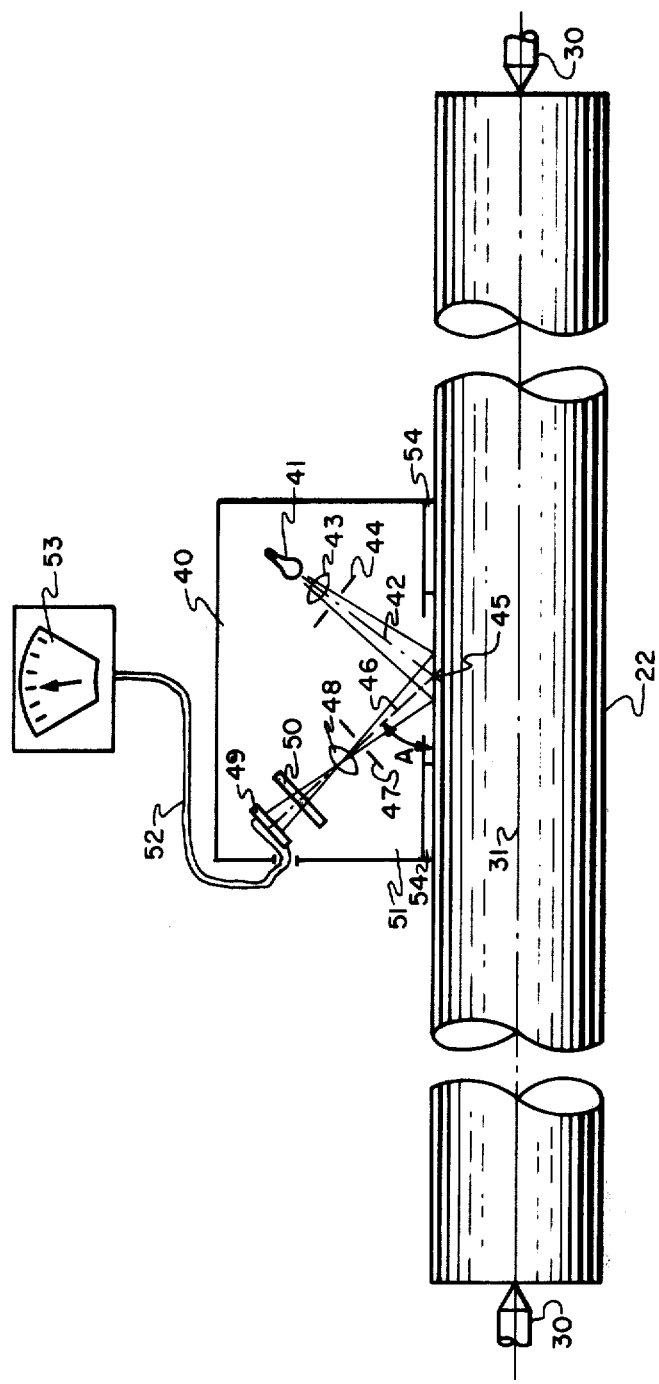
FIG. 2 schematically represents the measuring step of the present invention.

It is preparation of the surface texture for chill rolls 13 and 22 to which the present invention is directed. Such preparation is normally performed on a center turning grinding machine as represented by FIG. 2 which supports the roll 22 between spindles 30 for rotation about the roll axis 31. As the roll is rotated between the spindles 30, an independently powered grinding wheel or belt traverses the roll 22 length.

Normally, the grinding process is performed in several sequences starting with a coarse grit abrasive wheel or belt for rapid material removal followed by increasingly finer abrasive grits until the desired ground finish is achieved.

Further surface preparation is by polishing which differs from grinding by the nature of the tool wheel and the abrasive. Polishing is often performed with an extremely fine grit, unconsolidated abrasive which is rubbed against the roll surface by a rotating cloth or elastomer wheel. There are also other techniques for accomplishing the same end.

As the roll surface is increasingly polished, an objective measure of the degree of polish becomes more obscure by prior art methods. Consequently, such finishes are categorized by more subjective nonmenclature as "dull," "matte," "satin," "mirror" and "high" gloss finishes. These are specular gloss qualities and are more strongly influenced by the light reflective profile of the surface than by the depth and frequency of surface irregularity as measured by the standard machinist's profilometer.

Briefly, specular gloss is measured by means of a glossmeter 40 (FIG. 2) which comprises a calibrated light source 41 for emitting a collimated incident beam 42 through a lens 43 and aperture 44.

The beam 42 is focused on the test surface to illuminate a target area 45 of precise dimension. Spectural reflection 46 from the target area 45 at a predetermined angle A is collimated through an aperture 47 and focused through a lens 48 upon the sensitive surface of a photocell 49.

A filter 50 may also be interposed in the light path for color compensation.

A shroud 51 encloses the optical components of the system to shield stray light sources.

The photocell power leads 52 are connected to an ammeter 53 or other measuring indicators for objective measurement of the light quantity reaching the photocell 49.

From the foregoing description it will be seen that the incident and reflective light paths 42 and 46 follow respectively divergent axes from a focal point on the test surface. Cosequently, these divergent axes define a plane which, in the present method is to be oriented to parallel coincidence with the roll axis 31.

For purposes of instrument calibration and invention use, a given glossmeter is used to measure the surface gloss quality of several chill rolls and the product issuing therefrom. Such measurements are all made at a given reflectance angle which, with an instrument such as Hunterlab D48D modular glossmeter manufactured by Hunter Associates Laboratory, Inc. of Fairfax, Va., may have selective increments of 20°,60° and 85°.

Calibration data as described above is presented graphically by FIG. 3. Such data was taken with the Hunterlab D48D glossmeter at 60° from 24 and 30 inch diameter steel chill rolls and 0.018 caliper bleached paperboard having a 0.75 mil thickness of polyethylene surface film coating.

Additional data of the type described above was taken relative to 35 inch diameter chill rolls and 0.5 to 1.0 mil film thickness on paperboard ranging from 0.014 to 0.028 caliper. Such data showed the relationship between roll surface and film surface texture to be independent of these parameters.

Figure 3:
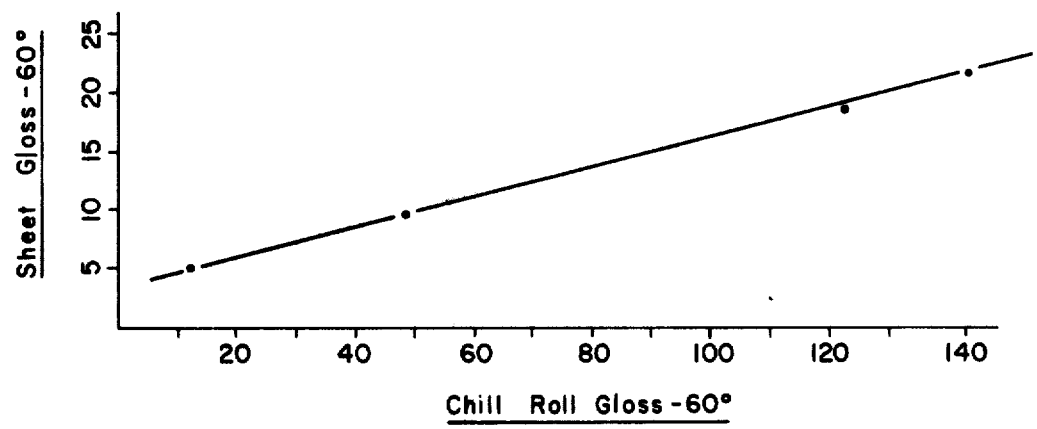
FIG. 3 graphically illustrates the correlation between surface texture glossmeter measurements respective to a chill roll surface and resultant film coated sheet product.

From the calibration data of FIG. 3, a chill roll may be polished to a determinable degree whereby the resultant plastic film product therefrom may be predicted.

In practice of the present method, it may be convenient to utilize the capacity of a profile measuring device to hone the subject roll surface to an efficient degree for subsequent polishing. Obviously, less effort is required to polish a relatively smooth ground surface than a rough turned roll surface to a "mirror" finish. However, for many applications, there is a point of diminishing returns beyond which further and finer grinding will not substantially reduce the requisite polishing effort.

Often there is a broad range of profile measurement within a given gloss may be developed. In these cases, no profilometer measurement is necessary in operations subsequent to an initial technique developed with a particular roll material. Polishing may proceed after grinding with a predetermined abrasive wheel or belt without regard to the profile result.

Figure 4:
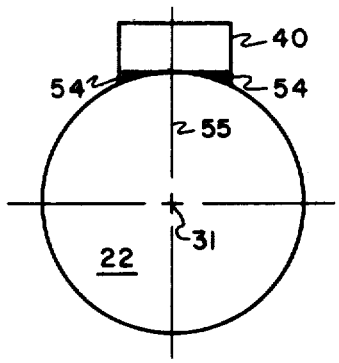
FIG. 4 schematically illustrates the axial end view of a cylinder having a glossmeter operatively positioned thereon.

For purposes of practice, a glossmeter to be used with the present invention may be modified with alignment pads 54 on the base thereof as best seen from FIG. 4. Such pads 54 are sized to the roll 22 diameter to positively confine the optical axis plane 55 of the instrument as defined by light axes 42 and 46 with the roll axis 31. Although alignment pads 54 are shown on both sides of plane 55, a completely stable and consistent alignment may also be achieved from the provision of pads on only one side of the optical plane. An obvious extension of providing alignment pads on only one side of the optical axis plane is to further provide a calibrated extension means for such pads to facilitate accurate alignment of the same instrument on the surfaces of rolls having different diameters.

The stability and convenience of alignment pads 54 notwithstanding, experience has proven that satisfactory results may also be obtained in the absence of any alignment pads 54 by simply rocking the instrument about the crown of the roll 22 periphery and relying upon the maximum gloss indication resulting from the ammeter 53.

In view of the foregoing description, as my invention, I claim:

1. A method of testing the surface texture of a chill roll having a cylindrical surface of revolution about an axis for casting a film of thermoplastic material thereagainst, said method comprising the steps of:
    obtaining co-relative spectral gloss data from the surfaces of representative chill rolls and respective plastic films cast thereagainst;
    calibrating a gloss meter having incident and reflective optical axes converging in an optical plane at an illumination test area, said calibration corresponding to said corelative spectral gloss data;
    positioning said glossmeter on the surface of a cylindrical test roll with said optical plane aligned to substantially parallel coincidence with the cylindrical axis of said roll;
    correlating the response measure of said glossmeter to said spectral data to determine the expected surface texture from plastic film that may be cast against said test roll.

2. An apparatus for measuring the spectral gloss of a cylindrical surface of revolution about an axis, said apparatus comprising a collimated light beam focused to a predetermined area on a test surface at a determined distance from an instrument test base, the luminous power of reflections from said area along a predetermined path being measured by photo-detector means, the axes of said collimated bean and reflection path converging to a point in said focal area and defining an optical plane, the improvement comprising test base orienting means to stabilize said apparatus on a cylindrical surface in a position whereby said optical plane is substantially parallel coincident with the axis of revolution of said surface.

3. An apparatus as described by claim 2 wherein said test base is a planar surface disposed substantially normal to said optical plane and said orienting means comprises at least one abutment member secured to said test base laterally of said optical plane.

* * * * *